United States Patent [19]

Manley

[11] Patent Number: 4,708,958

[45] Date of Patent: Nov. 24, 1987

[54] 6-(IMIDAZOLYLPHENYL)-4-IMINOPYRIMIDINONES USEFUL AS HYPOTENSIVE AGENTS

[75] Inventor: Paul W. Manley, Monks Risborough, United Kingdom

[73] Assignee: G. D. Searle & Co., Chicago, Ill.

[21] Appl. No.: 911,927

[22] Filed: Sep. 24, 1986

[51] Int. Cl.$^4$ .................. A61K 31/415; C07D 239/10
[52] U.S. Cl. ..................................... 514/274; 544/317
[58] Field of Search ......................... 544/317; 514/274

[56] References Cited

FOREIGN PATENT DOCUMENTS 123402 10/1984 European Pat. Off. ............. 544/310
0166564 1/1986 European Pat. Off. ............. 544/317

Primary Examiner—Alan L. Rotman
Assistant Examiner—J. Richter
Attorney, Agent, or Firm—Paul D. Matukaitis; J. Timothy Keane

[57] ABSTRACT

This invention relates to novel 6-(imidazolylphenyl)-4-iminopyrimidinone compounds having antihypertensive and platelet aggregation inhibition activity.

More particularly, the present invention relates to a novel class of pyrimidinone derivatives represented by the formula

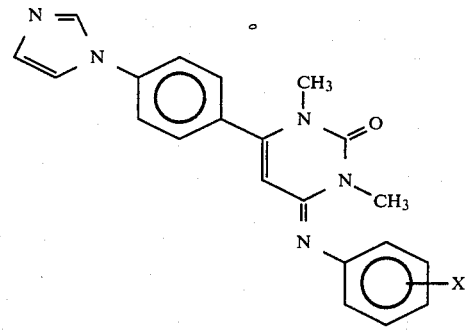

and the pharmaceutically acceptable salts thereof wherein X may be one to three substituents selected from the group consisting of R,—OR,—SR,—NHR,—NR$_2$, Cl, Br, F, NO$_2$,—COCH$_3$, —COOH,—COOR,—CONHR,—CONR$_2$, and —OH; and where R represents lower alkyl having 1-6 carbon atoms.

4 Claims, No Drawings

6-(IMIDAZOLYLPHENYL)-4-IMINOPYRIMIDINONES USEFUL AS HYPOTENSIVE AGENTS

BACKGROUND OF THE INVENTION

1. Field of the Invention

This invention relates to 6-(imidazolylphenyl)-4-iminopyrimidinone, its pharmaceutically acceptable salts, and derivative compounds which exhibit antihypertensive activity and the ability to inhibit platelet aggregation factor. The compounds are useful as blood pressure regulators and anti-platelet agents.

2. Description of the Related Art

Fujisawa, European Patent Publication No. 123,402 describes the synthesis of pyrimidine compounds and indicates their usefulness as cardiotonic, antihypertensive cerebrovascular, and anti-platelet agents.

The present invention differs from the prior art in that the compounds of the present invention have an unsaturated heterocyclic ring (imidazole) attached to the 6-phenyl ring and are therefore structurally distinct. The prior art neither teaches nor suggests that the presence of an imidazole ring conjugated to the pheny ring of 6-phenyl-4-iminopyrimidinone compounds would produce a potent antihypertensive or anti-platelet agent.

SUMMARY OF THE INVENTION

This invention relates to novel compounds of the formula

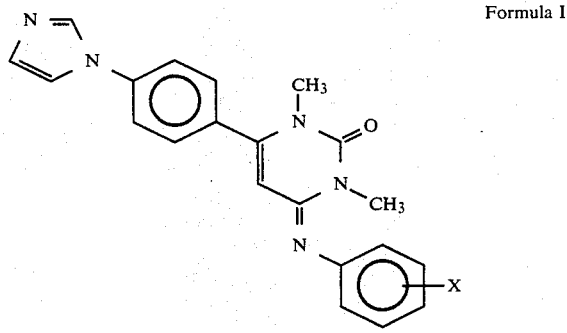

Formula I and the pharmaceutically acceptable salts thereof wherein X may be one to three substituents selected from the group consisting of R, —OR, —SR, —NHR, —NR$_2$, Cl, Br, F, —NO$_2$, —COCH$_3$, —COOH, —COOR, —CONHR, —CONR$_2$ and —OH and wherein R represents lower alkyl having 1–6 carbon atoms.

The compounds of the invention are useful because they possess pharmacological activity in animals. More particularly, the compounds of the invention exhibited antihypertensive activity. The compounds of the invention also exhibited the ability to inhibit platelet aggregation factor (PAF) as determined by the platelet dysfunction test.

DETAILED DESCRIPTION OF THE INVENTION

The invention encompasses compounds of Formula I which are prepared by arylating a starting material such as 3,4-dihydro-6-(4-fluorophenyl)-1,3,dimethyl-4-phenylimino-2(1H)-pyrimidinone with excess sodium imidazolide in DMSO in the presence of heat, whereby the fluoro group on the 6-phenyl ring is substituted by the imidazolyl group to produce 3,4-dihydro-6-(4-imidazolylphenyl)-1,3-dimethyl-4-phenylimino-2(1H)-pyrimidinone.

Production of the starting material possessing the fluoro group on the 6-phenyl ring has been described by Fujisawa, European Patent Publication No. 123-402.

By varying the substituents on the 4-phenyl ring, the necessary variations in X can be achieved to produce the compounds of Formula I.

In the compounds of Formula I, R refers to straight and branched chain alkyl having 1–6 carbon atoms such as methyl, ethyl, propyl, butyl, isobutyl, pentyl, isopentyl, and the like.

The compounds of Formula I may be administered as pharmaceutically acceptable addition salts. Such salts are readily prepared in the conventional manner. Suitable pharmaceutically acceptable salts include organic acid salts such as the fumarate, maleate, tartrate, (methane-, ethane-, and benzene) sulfonates, citrate, and the malate; and mineral acid salts such as the hydrochloride, hydrobromide, and sulfuric.

The compounds of the invention possess biological activity in animals. In particular, the compounds of the invention exhibited antihypertensive activity as determined by a pressor test conducted on rats and anti-platelet activity as determined by the ability to inhibit platelet activation factor.

In the pressor test, rats were continuously infused with the vasoconstrictor, angiotensin II, at a dose of 100 mg/0.1 ml/min which increased their blood pressure relative to a control group. During the infusion with angiotensin II, a single dose (10 mg/Kg) of a compound of the invention, 3,4-dihydro-6-(4-imidazolyl phenyl)-1,3-dimethyl-4-phenylimino-2(1H)-pyrimidinone (Formula II) was simultaneously administered with the angiotensin and the resulting decreases in systolic and diastolic blood pressure were recorded at 1, 5, 10, 20, 30, and 60 minutes after dosing. The systolic and diastolic blood pressures for each animal for each recording period were added together and the average individual blood pressure for each recording period was determined. The individual blood pressure were then compared relative to the mean blood pressure of the control group and this data is summarized in Table I.

Table I indicates that the compounds of Formula II was effective in reducing the blood pressure in hypertensive rats within the first minute after infusion and remained effective for at least 60 minutes after dozing despite continuous infusion with the vasoconstrictor and agonist angiotensin II.

TABLE I

RAT BLOOD PRESSURE RELATIVE TO THE CONTROL GROUP (Mean IS.D.)

| | Angiotensin II | | | | | |
|---|---|---|---|---|---|---|
| | Minutes After Infusin Of Formula II | | | | | |
| | 1' | 5' | 10' | 20' | 30' | 60' |
| mm Hg | +21.5 ± 0.9 | −47 ± 3.9 | −57.8 ± 2.8 | −61.5 ± 2.6 | −68 ± 4.0 | −69 ± 4.7 | −64.5 ± 7.4 |

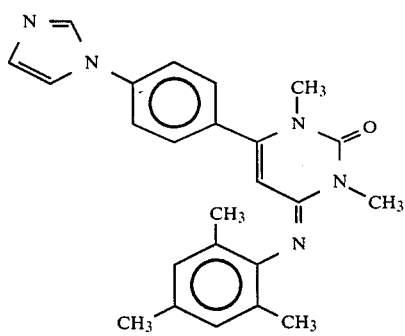

Formula II

In the platelet dysfunction test, human venous blood was collected from healthy male donors, who had denied any medication during the previous 14 days. Nine volumes of blood were mixed with one volume of 3.24% trisodium citrate. The citrated blood was centrifuged at 160 g for ten minutes at 22° C. to obtain platelet rich plasma (PRP). The platelets were then counted on a Coulter counter, and the platelet count was adjusted to 200,000 per µl with plasma. The PRP was then treated with indomethacin dissolved in dimethylsufoxide (10 µg indomethacin per ml PRP). A stock solution of PAF ($C_{16}$ or $C_{18}\beta$-acetyl-$\gamma$-O-alkyl-L-$\alpha$-phosphatidylcholine; 1 mg/ml) was prepared as a solution in chloroform-methanol (9:1 v/v). A 10 µl portion of the stock solution was evaporated to dryness under nitrogen and dissolved in 0.15M sodium chloride-0.15M tris.HCl (90:10 v/v) buffer containing 0.25% bovine albumin. Small volumes of the PAF solution (5–15 µl) were added to 0.5 ml samples of indomethacin-treated PRP and the aggregation trace was recorded using an aggregometer. A dose response curve was obtained and a sub-optimal dose of PAF was determined for use in inhibition studies.

Indomethacin-treated PRP (0.5 ml) was incubated with a test compound dissolved in buffer (ca. pH5) or dimethylsulfoxide for two minutes at 37° C. prior to addition of the sub-optimal dose of PAF. The subsequent aggregation trace was recorded and the percent inhibition of PAF primary aggregation was determined by comparison with a control PAF-induced aggregation trace. (Due to variability in PAF-induced aggregation within a given PRP samnple, a control PAF-induced aggregation was determined every two or three samples.) An inhibition does-response curve was determined for Formula II of this invention and the $IC_{50}$ value calculated. (A $IC_{50}$ is the concentration of Formula II which will inhibit the aggregation of 50% of the platelets which have been induced to aggregate by PAF.) Table II lists the $IC_{50}$ for formula II of this invention.

TABLE II

| PAF-INDUCED PRIMARY AGGREGATION IN HUMAN PLATELET-RICH PLASMA | |
|---|---|
| Compound. | $IC_{50}$ µM |
| Formula II | 2.4 |

For the above-mentioned use, the dosage administered will vary depending upon the compound employed, mode of administration and treatment desired. Accordingly, the compounds of Formula I or their pharmaceutically acceptable acid addition salts may be used as medicaments. Medicinal preparations such as tablets, capsules, dragees, granules, suppositories, or injectable solutions or suspensions for enteral or parenteral administration are suitable. Moreover, aside from the usual organic or inorganic pharmaceutically acceptable adjuvants, e.g., lactose, starch, talc, stearic acid, water, alcohols, natural or hardened oils, and waxes, these preparations may also contain suitable preserving, stabilizing, or wetting agents, solubilizers, sweetening or coloring substances and flavorings.

Similarly, the invention also provides a pharmaceutical composition comprising as an active agent, a compound of Formula I or a pharmaceutically acceptable acid addition salts thereof in association with a pharmaceutical carrier or diluent.

In the following example, all temperatures are indicated in degrees, centigrade and are uncorrected. This example is given by way of illustration only and is not to be construed as limiting the invention either in spirit or in scope, as many modifications in materials and methods will be apparent from this disclosure to those skilled in the art.

DESCRIPTION OF THE PREFERRED EMBODIMENTS

Example 1

(3,4-dihydro-6-[4-(1H-imidazol-1-yl)phenyl]-1,3-dimethyl-4-[2,4,6-trimethylphenyl)imino]-2-(1H)-pyrimidinone (Formula II)

To a solution of 190 mg of 3,4-dihydro-6-[4-fluorophenyl]-1,3-dimethyl-4-[(2,4,6-trimethylphenyl)imino]-2-(1)-pyrimidinone (0.54 mmol) in approximately 6 ml of DMSO was added 150 mg of sodium imidazolide (1.67 mEq) with stirring and the reaction mixture was heated to 170° C. for several hours. The reaction mixture was determined by TLC to be 50% complete. A further 50 mg of sodium imidazolide (0.55 mEq) was added and the reaction mixture was heated at 170° C. for two hours at which time an additional 80 mg of sodium imidazolide (0.88 mEq) was added and the reaction mixture was heated at 170° C. for approximately 24 hours.

To the cooled reaction mixture was added 120 ml of ethyl acetate. The diluted reaction mixture was washed 5 times with water, dried, filtered, and the solvent evaporated under vacuum. The remaining residue was purified by passing it through a column of silica gel and sequentially eluting with $CH_2Cl_2$; $CH_2Cl_2$:$CHCl_3$ (50:50); and $CHCl_3$.

After eight hours, 150 mg of the purified product represented by Formula II passed through the column and was dried under nitrogen, M.P. 93°–96° C.

While the present invention has been illustrated with the aid of certain specific embodiments thereof, it will be readily apparent to those skilled in the art that the invention is not limited to these particular embodiments and that various changes and modifications may be made without departing from the spirit of the invention or the scope of the appended claims.

What is claimed is:

1. A compound of the formula

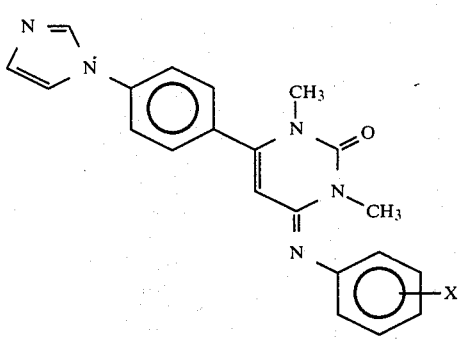

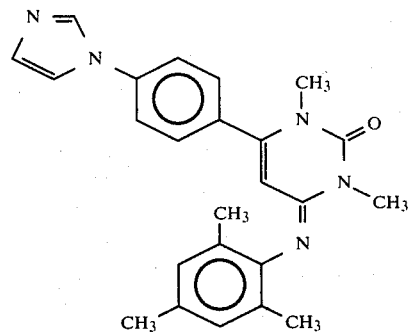

and the pharmaceutically acceptable salts thereof wherein X represents one to three substituents selected from the group consisting of R, OR, SR, NHR, NR₂, Cl, Br, F, NO₂, COCH₃, COOH, COOR, CONHR, CONR₂, and OH and wherein R represents lower alkyl having 1-6 carbon atoms.

2. A compound according to claim 1 which is 3,4-dihydro-6-[4-(1H-imidazol-1-yl)phenyl]-1,3-dimethyl-4-[(2,4,6-trimethyl phenyl)imino]-2(1H)-pyrimidinone.

3. A method of treating hypertension in animals comprising administering to a hypertensive animal a therapeutically effective anti-hypertensive amount of a compound of the formula and the pharmaceutically acceptable salts thereof wherein X represents one to three substituents selected from the group consisting of R, OR, —SR, —NHR, —NR₂, Cl, Br, F, NO₂, —COCH₃, —COOH, —COOR, —CONHR, —CONR₂, or —OH and wherein R represents lower alkyl having 1-6 carbon atoms.

4. A method of treating hypertension according to claim 1 comprising administering to a hypertensive animal a therapeutically effective antihypertensive amount of 3,4-dihydro-6-[4-(1H-imidazol-1-yl)phenyl]-1,3-dimethyl-4-[(2,4,6-trimethylphenyl)imino]-2(1H)-pyrimidinone or the pharmaceutically acceptable salts thereof.

* * * * *